United States Patent [19]
Farrell et al.

[11] Patent Number: 5,609,724
[45] Date of Patent: Mar. 11, 1997

[54] FUNGI FOR PITCH REDUCTION AND THEIR PREPARATION

[75] Inventors: Roberta L. Farrell, Danvers, Mass.; Yitzhak Hadar, Rehovot, Israel; Philip A. Wendler, Belmont; Wendy Zimmerman, Watertown, both of Mass.

[73] Assignee: Sandoz Ltd, Basel, Switzerland

[21] Appl. No.: 469,535

[22] Filed: Jun. 6, 1995

Related U.S. Application Data

[62] Division of Ser. No. 131,260, Oct. 1, 1993, Pat. No. 5,476,789, which is a continuation of Ser. No. 657,581, Feb. 19, 1991, abandoned, which is a continuation-in-part of Ser. No. 560,521, Jul. 31, 1990, abandoned.

[51] Int. Cl.$^6$ ........................................ D21C 1/00
[52] U.S. Cl. .................. 162/72; 162/1; 162/DIG. 4; 162/DIG. 12
[58] Field of Search .................. 162/1, 72 B, DIG. 12, 162/72, 199, DIG. 4

[56] References Cited

U.S. PATENT DOCUMENTS

| | | | |
|---|---|---|---|
| 3,486,969 | 12/1969 | Nilsson et al. | 162/72 B |
| 5,176,796 | 1/1993 | Irie et al. | 162/174 |

FOREIGN PATENT DOCUMENTS 854696  8/1993  Canada.

*Primary Examiner*—Peter Chin
*Attorney, Agent, or Firm*—Robert S. Honor; Carl W. Battle; Michael P. Morris

[57] ABSTRACT

Ascospores of wood-penetrating, pitch-grading fungi of the class of Ascomycotina and Deuteromycotina, eg. Ophiostromas, may be screened to provide fungi combining the properties of good growth on non-sterile wood substrates and minimized or even enhanced brightness effects for use in pitch reduction of wood substrates, eg. logs and wood chips. A new and improved method of isolating such ascospores involving effective suspension in an oil consumable by the fungus, eg. a vegetable oil, and then treatment of the oil with a dispersing agent is also disclosed.

3 Claims, No Drawings

FUNGI FOR PITCH REDUCTION AND THEIR PREPARATION

This is a division of application Ser. No. 08/131,260, filed Oct. 1, 1993, now U.S. Pat. No. 5,476,789, which in turn is a continuation of application Ser. No. 07/657,581, filed Feb. 19, 1991, which in turn is a continuation-in-part of application Ser. No. 07/560,521, filed Jul. 31, 1990, the latter two of which are now abandoned.

This invention relates to fungi having particularly desirable overall properties for reducing the pitch content of pulpwoods and to the preparation of such fungi.

In copending U.S. application Ser. No. 310,814, filed Feb. 13, 1989 and its soon to publish foreign counterparts, there is described the use of certain wood-penetrating fungi useful in reducing the pitch content of pulpwoods.

Such fungi are applied or distributed upon pulpwood forms such as wood chips, sawdust or logs, or first stage mechanical pulp, and the resulting treated substrate maintained under conditions under which the fungus grows, for a time sufficient to reduce the pitch content of the pulpwood. The invention is judged of considerable importance in reducing the substantial amount of downtime caused by pitch deposits and accumulations in the pulp and paper and other industries which convert pulpwoods. Improved physical or strength properties of ultimate products such as paper are also indicated.

The fungi found to be useful for such purposes are wood-penetrating fungi of the fungal classes Ascomycetes and Deuteromycetes, more particularly in a wide variety of genera which comprises the genera classified in the subclass Ophiostomatales as well as the genera including the imperfect states associated to Ophiostomatales. Examples of such Ophiostomatales genera include without limitation Ceratocystis, Ceratocystiopsis, Graphium, Leptographium, Ophiostoma, Phislocephala and Sporothrix as defined with reference to the generic concepts stated in Harrington T. C., New combinations in Ophiostoma or Ceratocystis species with *Leptographium anamorphs*, Mycotaxon, 1987, 28:39–43 and in Leptographium Species, Their Distributions, Hosts and Insect Vectors, Harrington T. C. & Cobb F. W., 1988, pages 1–39, APS press, St. Paul, Minn., as well as Rhinocladiella and Hyalodendron as defined with reference to Hawksworth et al. Ainsworth and Bisby's Dictionary of Fungi, 1983, 7th edition, Commonwealth mycological institute, Kew, Surrey, England. Other Examples of genera (not classified as Ophiostomatales) in which penetrating fungi are found on a limited species basis include Alternaria, Cadophora, Chloridium, Diplidia, Dactylella, Fusarium, Hormodendron, Hormonema, Phialophora, Sphaeropsis, Trichosporium, Codinaea and Valsa as defined with reference to Hawksworth, et al. (supra). Preferred fungi are found in the genera Chloridium, Dactylella, Phialophora and Valsa as well as in the genera classified as Ophiostomatales or the imperfect states associated with Ophiostomatales, these latter genera being particularly preferred. More preferably, the fungi are found in the genera Ceratocystis, Ceratocystiopsis, Graphium, Leptographium and Ophiostoma, this latter being mostly preferred.

The indicated fungal classes encompass many so-called staining fungi, and in particular the deep staining or penetrating stain fungi which can infest harvested wood in many locations and which, ironically, have long been considered a tolerable nuisance or object of suppression by industry.

The fungi within the above-indicated fungal classes which may be used include not only the typical representatives of the classes, their genera and individual species, but also include all of individual strains, isolates, variants, mutants and the like which penetrate wood and degrade pitch.

It is generally within the skill of the art to provide or isolate strains or variants representing less common strains or variants of the same species, or to produce mutants, for purposes of obtaining those better suited for practical use. Hence, different strains or variants exist in nature and may be isolated in various ways. For example, a so-called "faded" or less colored strain of a typical dark-staining species may exist or arise spontaneously in an older, eg. 5–9 day old culture, of the dark staining fungus and appear as a grayish spot(s) after plating of the culture, eg. as done for serial dilution. Such spots may be picked out and grown as individual isolates, to provide a variant strain also useful to reduce pitch.

Also, penetrating fungi, eg. blue stain fungi, are usually heterokaryotic. In the course of culturing, the nuclei segregate in cells in various combinations which change the characteristics of the strains. Variants formed in this manner may be isolated. Also, homokaryotic or ascospore cells or strains may be selected and cultured and could be recognized as being preferred for use in said invention as the characteristics of such strain or homokaryotic cells are stable. For example, ascospores of heterokaryotic strains are, by definition, homokaryotic. Spores may be recovered and individually separated, eg. plated on a solid growth medium at a dilution which allows growth, by known procedures. The resulting strains are tested for homokaryotic nature and evaluated as to overall desired properties, eg. pitch reduction.

The indicated prior invention was initially made with reference to certain true blue stain fungi and various isolates which embody very desired capabilities for use in the invention including ability to grow and penetrate wood substrates under non-sterile, essentially competitive growth conditions. A later, blue stain isolate, herein TAB 28, became our standard. The one application drawback of a true blue or dark staining fungus is that it colors or stain the wood, typically a dark gray or black blue or black (these colors being sometimes tinted). Such dark staining, which can be measured by brightness evaluations, may result in the need to increase the degree of bleaching of certain pulps at a later stage although such increase is relatively minor and any added expense far less than the savings from the pitch reduction. We nevertheless searched for or evaluated lighter colored fungal species or variants, including faded variants we were able to literally pick from cultures of the dark staining fungi. Such variants which could grow up as lighter colored fungi and resulted in less or even minimum coloring effect on treated wood, compared to the original fungus in the culture. While such "faded" isolates were also useful in accord with said prior invention, such faded isolates and also cultures of different penetrating, pitch-degrading fungi which are lighter staining or do not stain at all seemed to lack the overall virulence on non-sterilized wood that made the dark staining fungi preferred candidates for practical use. Hence, the lighter fungi would generally require much higher doses and/or longer treatment times in order to approach the results obtained on non-sterile wood with the darker growing species or members of the same species, even though the faded isolates performed well on sterilized substrates. While the faded isolates indicate that the properties associated with production of a dark or blue stain are not essential for pitch reduction, it was uncertain whether such properties might be associated with the competitive growth capability on non-sterile substrates which made the darker or blue stain fungi the preferred fungi.

In particular, melanin production is generally associated with the dark staining ability of the fungi in question and melanin is indicated to be associated with certain properties which have made the dark staining fungi preferred candidates, and in particular the virulence or competitive growth capability of such fungi in the non-sterile environment existing in harvested wood forms used as raw materials by industry.

In a continuing effort to find fungi or fungal isolates which might approach the desired properties of darker staining fungi but which grow lighter in color and have reduced or even essentially minimum or no coloring effect on the wood, a program founded on the well-known technique of ascospore isolation and selection was instituted. During this program an improved method for isolation of such ascospores was developed and it was found that homokaryons having reduced negative brightness effects but substantially equal virulence or growth ability on non-sterile substrates compared to the parent fungus can be produced, typically as a very small number of Ascospore isolates among a large number which are generated. Homokaryons having equal or enhanced brightness effects but better virulence on non-sterile substrate can similarly be produced. Two isolates having minimum or no negative brightness effects and very good competitive growth capability were found and are described below. At least one of these is indicated to even potentially improve brightness on non-sterile substrates which in the absence of any treatment would suffer significant brightness loss during storage as a result of natural fungal infestation.

The ability to provide wood-penetrating, pitch-degrading fungi having substantially no negative brightness effects but other desired properties approaching or equally those embodied for practical use of the preferred blue stain TAB 28 is also indicated.

One aspect of the present invention, therefore, involves the method of providing wood-penetrating fungi for reducing the pitch content of wood substrates comprising: a) isolating ascospores of a culture of one or more wood-penetrating, pitch-degrading parent fungi of the class of Ascomycotina or Deuteromycatina; and b) selecting any one or more homokaryotic fungi provided by the ascospores that are characterized by the criteria of i) growing on a sterilized wood substrate to reduce the pitch content of the substrate by at least 20% after no more than 21 days growth, preferably no more than 14 days growth, and which are further characterized by either or both of the criteria of ii) affecting brightness of the same, sterilized substrate after 21 days growth negatively to no greater extent than a referenced parent fungus (if there is more than one parent, only one need be referenced for comparison) while growing more virulently than on the parent on the same but non-sterile wood substrate as determined over a growth period of 10 days, or iii) producing a higher brightness level or value on the sterilized substrate than the parent fungus after 21 days growth while growing substantially no less virulently than the parent on the non-sterilized substrate as determined over a growth period of 10 days. The invention also provides the method of applying an inoculum obtained from such a homokaryotic fungi, or the progeny or a derivative of such fungi, to a pulpwood substrate or first stage mechanical pulp for a time sufficient for the fungus to grow and to reduce the pitch content of the substrate or pulp.

Basically, it has been found that melanin content or production level of the fungi in question can be overcome as a factor controlling virulence by the process of ascospore selection to provide improved fungi for pitch-degradation use, either by providing greater virulence on non-sterilize substrates while at least retaining existing brightness level effects of the parent fungus, but particularly by providing fungi which produce enhanced brightness levels, as can be determined on a sterilize substrate, while growing substantially no less virulently on the non-sterile substrate. Such homokaryotic fungi can be highly effective and desirable for use in pitch-reduction, particularly on non-sterile substrates, and can act effectively in practical use after no more than 14 days growth at inoculation levels not exceeding $10^{10}$ CFU (colony forming units) per Kg. of substrates, such as refined pulpwoods, and can even be effective after no more than 10 days growth at such inoculation level. Fungi provided by the invention process are indicated to be generally novel on a species by species basis, ie. new within each species type, as are certain particularly preferred ascospore derived fungi which can be defined differently and in relation to their more absolute effects on brightness on non-sterile pulpwood.

Non-sterile substrates are typically infected with a wide variety of microorganisms and in many cases infected with fungi of widely varying types which can stain or color the wood, including in some cases blue stain fungi which may grow in time, and often rather quickly. All such coloring or staining fungi (or other organisms) will color the wood (in any of a variety of colors such as black, blue of different shades, reds, greens and orange) and bleaching treatments are usually adjusted by adding bleaching agents to overcome such effects when encountered to a significant degree, at least with mechanical pulps. The use of a penetrating fungus to degrade pitch may increase bleaching requirements when the fungus itself imparts or leaves a medium to dark color on the wood. By the present invention it is not only possible to obtain fungi which grow rapidly at efficient inoculation levels on non-sterile wood, while reducing negative brightness effects relative to the parent, pitch-degrading parent fungi, but it is indicated, in accord with a particular preferred objective and embodiment, that the brightness of the wood substrate can not only be minimally effected or substantially unaffected relative to untreated, non-sterile controls (representing a typical commercial wood chip pile) but can even be enhanced compared with such a control. Such particularly preferred fungi and their use on non-sterile substrates, including those which might be moderately or even greater naturally infected with coloring or staining fungi, are viewed of great interest and practicality since pitch can not only be reduced with its attendant cost savings and improved paper/product strength properties, but the brightness of the treated substrate may be even enhanced relative to untreated pulpwood as normally entered into a pulping process. While such brightness benefit may be due to a minor extent to a light or substantially white residue remaining from the mycelia of particularly preferred fungi, such benefit is indicated to be largely provided by the ability of the preferred fungi to grow into or exclude other coloring fungi or organisms in locations where such other organisms would otherwise grow over the treatment period, eg. 14 days. Non-sterile pulpwood treated with such particularly preferred fungi are also considered novel since it is indicated that such substrates treated with other very light growing or faded fungi having the reduced virulence or competitive growth (relative to their own coloring effect) we have experienced, even when inoculated at relatively high dosages, will act largely on locations where the native coloring fungi or other organisms will not spread and are insufficiently competitive to exclude enough of the growth of the nature coloring fungi to positively impact on brightness. Such novel pulpwoods and the fungi which produced them may be defined relative to natural infection with coloring fungi or organisms when a non-sterile control (untreated) sample exhibits sufficient infection that its brightness is reduced by at least ten percent (10%) at room temperature relative to sterile, untreated samples over the treatment period, whereas the novel fungal treated substrates have a brightness level at least equal to or greater than the brightness level of said non-sterile and untreated pulpwood control after the treatment period, eg. 14 days. Those fungal treatment substrates having improved brightness compared to the non-sterile, untreated control sample will be especially desired products for further processing, especially in the manufacture of mechanical pulp products.

The invention is particularly applied, but not limited to, ascospore selection from cultures of fungal species which have at least one dark or blue stain member or representative, including faded, gray color members or variants of such species, whether such ascospores arise from self-fertile species members or by the mating of species members. The term "parent fungus" as used herein means any fungus which produced the ascospores in culture. If two fungi are mated, for example, it means either of the two mating. If multiple mating types involved more than two mating types can combine, then it means any of the mated fungi. Most fungi involve only two mating types. Hence, if two or more parents are involved in producing the ascospore, any parent may be referenced for purpose of determining whether the screening criteria are met, providing the same parent is always referenced for all criteria in each evaluation of the ascospore in question. All parents will usually be individually referenced in a series of evaluations of each parent separately for each ascospore.

The fungi in question, including the blue (dark) stain fungal species (including their faded members) are generally presumed heterokaryotic, that is, they contain multiple nuclei each containing the full complement of genes necessary to complete the life cycle of the fungus. By allowing such fungi to sporulate under certain conditions, such as a solid culture, eg. on an agar plate, followed by isolating spores containing single nuclei (ascospores), and growing the ascospores as separate colonies (thus generating homokaryotic strains), candidates for screening are obtained. The isolated strains are then screened for desired properties. When a parent fungus is not self-fertile, it must be mated with an appropriate or compatible mating partner of the same species to provide ascospores, as is known in the art. All possible variations in procedures for obtaining ascospores may be used. Such basic procedures for such ascospore selection are well known although we provide an improved ascospore isolation procedure herein in connection with such fungi. Fungi entered into the procedure as parents may be pre-screened for desired properties.

Homokaryotic isolates, as in the case of fungi growing as homokaryotics, as well as heterokaryotes, may be mated by known technique to produce ascospore cultures. Any resulting homo-karyotic fungi may be mated with another member of the species, including its parent fungus, to provide ascospores for selection, provided appropriate mating types are indicated. The mating of such ascospore isolates may be with another ascospore isolate or with a wild type. Hence, it is well within the scope of the invention to use the initially obtained ascospore(s) to obtain other ascospores of desired improved properties, and to continue such generation of new ascospores by mating as desired.

The procedure may be applied to fungi of all colors, from white to black, whether or not individual strains or variants are self-fertile, as can be determined by known techniques. It is generally preferred to initially use the mating procedure when a true dark or blue stain (unfaded) strain is to be explored, desirably with one partner being the true blue stain and the other a lighter member. Prior to mating, the basic procedure may be used if desired with self-fertile strains to obtain accospore selected isolates for the mating. Thereafter, the resulting isolates may be also subjected to matings, subject to having appropriate mating types. For example, it is indicated that the light (light gray) isolate C1 det 5 (C-1D5), hereinafter, is suitable for mating with the true blue stain fungus TAB 28. Similarly, the light (essentially white) isolate C1 det 84 (C-1D84) can be mated with the blue (dark) stain or essentially black isolate TAB 51.

When a light or white growing ascospore isolate is to be further mated, it is preferred to mate it with a strain which is darker and more virulent than the lighter ascospore strain.

Hence, the invention includes not only individual ascospore isolates and their resulting fungi but also all of the additional derivatives obtainable therefrom, particularly those embodying at least the level of desired properties of the parent ascospore. A finally selected ascospore fungus may be mated to provide a heteroharyotic fungus for use in pitch degradation, but this is not preferred as the heterokaryons have been found to tend to be unstable in one or more desired properties during repeated growth or large scale growth. The Ascospore may also be mutated to provide other desirable derivatives, including man-induced mutations, and those which at least substantially embody the desired improved properties of the parent ascospore are also included in the invention.

Procedures for the generation, general separation, dispersal and individual isolation of ascospores and the growth and isolation of fungi they generate are well known. A representative literature reference is, for example, Upadhyay, H. P. (1981), A Monograph of Ceratocystis and Ceratocystiopsis; University of Georgia Press, Athens, pages 28–29. A publication with specific to ascospores of Ophiostoma is Brasier, C. M. and J. N. Gibbs (1976), Inheritance of Pathogenicity and Cultural Characters in *Ceratocystis ulmi*: Hybridization of Aggressive and Non-Aggressive Strains; Ann. Appl. Biol. 83, 31–37. In general, the parent fungus (or fungi) is cultured to the stage where ascospore generation is sufficiently complete and the ascospores sufficiently liberated from the fungal mass or secreted that the ascospores as a mass or collection can be generally separated or recovered, for example, by picking all or one or more portions of the viscous, hydrophobic ascospore-containing material at the top of the perithecium with a sterile dissection needle and transferring to a specialized spore suspension medium such as pinene which will dissolve the hydrophobic material and free the spores into the suspension medium. The medium (or portions thereof) containing the ascospores is then diluted and the dilution spread on plates containing a suitable growth medium for development of a solid phase fungal growth in a manner which allows the ascospores to develop or grow into discrete or individual fungus colonies which can be picked or isolated for further growth in individual cultures, eg. liquid culture, to provide inoculum for evaluation of the fungus produced or generated from the individual ascospores.

Given our observations and literature indications that the chances of achieving our objectives, if existent at all, would depend upon screening a very large number of ascospore-generated fungi, our efforts were initially frustrated by the inability of pinene (and certain other approaches that were tried) to produce a large number of individual or discrete isolates for screening. In particular, the standard pinene procedure produced very few viable spores. As an aspect of the present invention, it was found that very high and suitable counts of viable ascospores of the subject pitch-degrading fungi may be obtained by taking up or dispersing the ascospores in their hydrophobic carrier as recovered from the fungal culture in a non-toxic oil which effectively dissolves the hydrophobic material to free the spores into the oil and which is consumable (as a food or carbon source) by the fungus, preferably a vegetable oil such as corn oil, and then treating the ascospore-containing oil with a non-toxic (to the fungus or its spores) oil dispersing agent which may be of any of the many known types for dispersing such oils, such as the well known Triton® X100. The spreading or plating out of the dispersing agent-treated oil results in large number of discrete, viable ascospore-containing droplets of said oil and, additionally, the oil is consumed and removed from plates as the fungus grows, leaving discrete fungal colonies which can be readily recovered and further cultured for evaluation. The large number of viable ascospore fungi obtained for screening by the indicated isolation method was important to ascertaining whether ascospore screening and selection could achieve our objectives, since considerable doubt existed and, as found in the experiment hereinbelow, only a very low percentage or number of a very large number of ascospore fungi were indicated to provide the sought-for improved properties.

Other Preferred Embodiments and General Evaluation Standards

A determination of whether or not the criteria of this invention are satisfied will be conducted on a laboratory scale. While reference may be made to the Experimental Section herein for guidance in certain cases, the determination will be made in accord with the description and discussion under the paragraph and the next two paragraph headings (Other Laboratory Evaluation Standards and Evaluation Procedures), and it is not represented that the experiments in the Experimental section conformed in particular aspects to such determination description.

With regard to criteria i), above, ie. pitch reduction, such evaluations are carried out on sterile substrates to eliminate the influence of other organisms which naturally infect non-sterile substrates. Generally, a pitch reduction of at least 20% in 21 days will be desired for the more suitable candidates. Reductions of at least 25%, particularly at least 30%, will generally indicate the preferred candidates. If criteria are met at 21 days, repeating the evaluations and achieving the level of at least 20%, 25% or 30% pitch reduction in 14 days will usually indicate the more preferred candidates.

One preferred group of ascospores for selection or initial selection, particularly when a parent is of a medium to dark gray, and the criteria are met, will be those producing an ascospore fungus which will reduce the pitch content of the substrate by at least 25% in not more than 21 days without decreasing the brightness level of the sterilized substrate by more than ten percent compared to an untreated, sterilized control.

With regard to criteria ii) and iii) and the evaluation concerning brightness, these evaluations are desirable conducted for screening purposes on sterile substrates to again eliminate the influence of organisms which naturally infect non-sterile substrates and obtain a more absolute assessment of the color influence of the candidate. These evaluations will also be conducted after growth for 21 days. When an improvement in brightness is the criteria, an improvement of at least about 5% is usually sought to reduce error and provide statistical confidence. The degree of improvement otherwise obtained may vary considerably. If a medium to dark color fungus is involved as a parent, improvements of the order of at least 10%, 15%, 20%, 25% or even more may be realized. If lighter parents are involved, lower orders of improvement may be realized, as would be the case when seeking to improve a previous ascospore isolate selected for brightness. Of course, no brightness involvement may be realized at all and criteria met when selection is to be made on the basis of growth virulence.

Growth virulence determinations in accord with criteria ii) and iii) will be conducted on a non-sterile substrate and made 10 days after inoculation to reflect the desired fungi provided by the invention. Such determinations are made as herein further described, on the basis of percentage of substrates or wood chips showing growth of the candidate compared to growth of the referenced parent. Such determinations may be made on a percentage basis and, when an improvement in virulence is the criteria to be satisfied, an improvement of at least about ten percentage points (ie. 80% to 90%) is usually sought to reduce error and provide statistical confidence. If the determination is to be made on the basis of virulence and both the referenced parent and candidate fungus show 80% or better growth, the evaluation/criteria dosage of $10^{10}$ CFU is reduced until the referenced parent growth is less than 70%, eg. 35–65%.

A determination of the satisfaction of criteria ii) and iii) may be dispensed in certain cases where certain ascospore fungi or their derivatives, desirably also a homokaryotic derivative, meet certain particularly preferred characteristics reflecting brightness and virulence on non-sterile substrate. In particular, desirable new fungi are provided by this invention when pitch reduction criteria are met on sterilized (and non-sterilized substrates) after 21 days as described above, and a control non-sterile substrate after 14 days is sufficiently influenced by native organisms that its brightness is reduced by at least 10%, especially by at least 20%, compared to a sterilized, untreated control, yet the ascospore derived fungus results in a brightness level, at the end of said 14 day period on the non-sterile substrate, which is at least as great as the brightness level of the untreated, non-sterile control. Such fungi are indicated to be novel relative to prior art fungi. A particularly desirable class of such fungi are those which actually increase the brightness, eg. by at least about 5% or more, compared to the untreated, non-sterile control. Preferred sub-classes of such fungi are those which effect either such desired result on at least one wood species or variety at dosages less than $10^{10}$ CFU/Kg., particularly at dosages not exceeding $10^9$, and especially dosages not exceeding $10^8$.

Especially preferred ascospore fungi provided by the invention are those showing at least about the same growth virulence as TAB 28 on a non-sterile substrate but which grow essentially white on the sterilized substrate, eg. a southern yellow pine substrate.

A suitable product form of the fungi of the invention is obtained by fluid bed drying of a mixture of a spore-containing fermentation concentrate, resuspended in water, and inert solid which does adversely affect the stability of the spores, eg. a clay such as Kaolin clay.

Other Laboratory Evaluation Standards

In carrying out the invention to isolate desired ascospore fungi meeting criteria in accord with the invention, various comparative evaluations will be made on pulpwood substrates to determine pitch reduction, brightness and virulence. These will be conducted on a laboratory scale. While the substrate may be of different pulpwood forms, we judge the criteria standard and more suitable form to be wood chips. The substrates will be obtained from fresh cut timber or logs stored at room temperature for seven (7) days immediately after cutting, and then made into wood chips which are promptly subjected to evaluation (or stored for a brief period at 5° C.). Wood chips showing after such seven days anything other than isolated or very minor visible growth of native fungi such as blue stains, *papulaspora* and *trichoderma* are rejected. Such substrates are selected to be free of knots. Each evaluation will be done on substrates of the same wood species and on substrate samples obtained from the same timber or log, and at the same time after cutting of the tree. A collection of such substrates exceeding evaluation requirement by at least 3 times will be thoroughly mixed to disperse isolated prices which may be naturally infected or more heavily infected with microorganisms. Individual sample lots of equal size (weight) and amounting to 200–400 grams each will be taken from the collection. Samples to be sterilized are heated in an autoclave at 120° C. for 45 minutes. Evaluations on non-sterile substrates may be started 7 days after cutting of the tree. Evaluations for comparison on sterile substrates are commenced at roughly the same time or slightly later, preferably after wood chips from the cuttings have been sterilized and allowed to completely cool to room temperature (ca 20° C.), at which temperature all evaluations will be made unless the referenced parent fungus optimally grows below 10° C., in which case the evaluations will be conducted in an environment stabilized at the optimum growing temperature. The inoculum will be applied as a concentrate or deionized water dilution from a culture at a inoculum concentration which together with the manner of using it to inoculate will not introduce more than about 1 ml. of water for each 100 g. of substrate. The dosage itself will be expressed in colony forming units representing the count by standard procedures of the total of viable mycelia and/or viable spores in the inoculum. The dosage applied will be same and not exceed the criteria maximum of $10^{10}$ CFU/kg. of substrate (prior to sterilization in the case of the sterilized sample). The inoculum will be in a form as similar as possible for the referenced parent fungus and ascospore fungus being evaluated. Hence, if the inoculum for one is essentially only mycelia, the inoculum for the other will be essentially only mycelia and harvested at an equivalent growth stage. In a like manner, mixtures of spores and mycelia will be in the same proportions. If the fungus can provide a high proportion of spores (75% or more of CFU) in culture, as is usually the case, an inoculum which is 75% or more spores of similar characterization will be used. Hence, if the fungus forms a high proportion of blastospores, such an inoculum will be used. The inoculation of the substrate will be done in a manner suited to contacting as many individual wood pieces as reasonably possible, even though initially only 10–30% of the chips may be actually contacted. The wood chip substrates will be placed in clear plastic bags of good size and the chips in the bag rested and spread out on a flat surface. The inoculum will be applied with an eyedropper by placing no more than one drop on individual chips. The bag is then sealed and the chips mixed/shaken thoroughly for 10 seconds to distribute the inoculum to other chips. The bag is then tightened or further closed around the chips if necessary to have good contact among chips in a pile-like accumulation. All inoculated substrates will be stored in the dark and then evaluated, the storage being done at room temperature except in the cases as indicated above. Each evaluation as above described will be run in triplicate and the results averaged, and each triplicate series will again be repeated three more times (total of four triplicate series) but using in each series samples from a different tree of the same species and variety within the same forest location. For obtaining the best fungi on a local or regional basis, it is preferred to isolate or derive the parent fungi from cut or dead timber or other pulpwood forms of the same species of wood respecting which the ascospore-derived fungus will be used in practical application, or otherwise conduct the evaluation on substrates of the use-targeted wood species type on which the parent was obtained or derived. If the wood species source of the parent fungus is unknown, a preliminary evaluation on sterile and non-sterile wood chips from several different wood species and varieties which the parent fungal species is known from the literature to infect will be conducted, and the evaluation will be conducted on the wood species or variety respecting which the parent fungus reveals the more vigorous growth. Ascospores-derived fungi meeting the criteria as above-stated relative to any referenced parent on any of the many currently known sources of pulpwoods, or on a targeted substrate wood species, will be new and useful in accord with the invention. The criteria are best met by the ascospore fungus when the substrate is the same wood species and variety from which the parent fungus may have been isolated on a regional basis.

Evaluation Procedures

A) The pitch content of substrates is determined in accord with the standard TAPPI Procedure T204 OS-76 and may be expressed as mg. of pitch content per gram of substrate which had been extracted with DCM (a.k.a methylene chloride). As used on a substrate such as wood chips, the treated chips are splintered with pruning shears to a width of about 1 cm, then dried overnight at 60° C. and then ground into sawdust using a Thomas-Wiley Intermediate Mill with a 10-mesh screen (10 gauge wire screen), and dried again overnight at 60° C. Three (3) grams of dried sawdust are combined with about 30 ml. of DCM and the resulting mixture agitated overnight (about 15 hours) at room temperature. The liquid medium is pipetted from the mixture, filtered through a 0.45 micron organic filter, the liquid allowed to evaporate at room temperature overnight (for about 15 hours) in a preweighed dish and the residue oven-heated at 60° C. for 30 minutes to further remove DCM. The weight of the residue is determined in mg. as the pitch content and expressed either as mg. of pitch content per gram of substrate or as a percentage of pitch in original the substrate (% extractives).

B) Substrate brightness is determined on 10 gauge sawdust and substrates such as wood chip will be first splintered using pruning shears to about 1 cm. and then ground using a Thomas-Wiley Intermediate Mill with a 10 gauge wire mesh screen, with intermediate dryings at 60° C. as indicated in A), above.

Brightness is measured on a Photovolt Reflection meter model 670. The meter is a separate unit from the photocell and the photocell can be turned upside down if desired. Using the above instrument, our procedure is as follows:

1. Calibrate the reflection meter with an enamel plaque calibrated in terms of paper brightness (75.0). Place the plaque on a petri dish and present it to the search unit (photocell). Adjust the meter reading to the value on the enamel plaque. The standard reading may be set this way or by placing the standard inside the petri dish so it is flush with the plastic. It is separated from the dish by any distance.

2. Fill the petri dish with an even layer of sawdust, about 10g or less, and present the dish to the search unit and take five readings from various regions of the dish. The average of the five readings is the brightness of the sawdust. A new petri dish is used for each sample and each replication.

C) Growth or virulence of a fungus will be measured for comparison among fungi and all possible conditions, unless otherwise specified, will again be made as identical as possible for the comparison. Growth or virulence is determined by a relatively simple visual observation protocol applied on a consistent basis, and carried out immediately at the end of the 10 day test period. The protocol is based on color categories of growth which can be observed or ascertained on each individual wood chip or substrate with the unaided eye at normal reading distance. One color category, typically the lightest, will represent the growth color of the ascospore candidate or lightest growing candidate if severl are to be compared with each other. Categories of white (w.), gray (g.) and black (b.) may be used as well as the five categories of white (w.), light gray (l.g.), medium gray (g.), dark gray (d.g.) and black (b.) depending largely on the color of ascospore candidate to be compared with its referenced parent fungus or the number of such candidates. The five color rating category is preferred as all candidates can be usually assigned into one of the five. The number of chips observed to have the color growth of the ascospore candidate is totalled in essentially four categories as used in the evaluations reported hereinbelow, viz. a single plus (+) is assigned when about 25% of the chips show growth of the particular ascospore candidate, two pluses (++) when about 50% show growth, three pluses (+++) when about 75% show growth and four pluses (++++) when about 100% show growth. If a percentage within about 5% points of an intermediate percentage, eg. 58% is within 5% points of 62.5%, a plus is added after a slash mark and the lower rating, eg. (++/+) or by (++/+++). In an analogous manner an intermediate rating below the first level rating is indicated by (+/−). A similar totalling will be made for the parent(s) to be referenced. For purposes of making more precise evaluations relative to the criteria described herein, when needed, an actual percentage will be determined and the percentages compared. However, a margin of error will be allowed for human error, the greater difficulty of ascertaining lighter growths and the substantial achievement of the objectives of the invention. Such margin is 10 percentage points, such that an ascospore candidate found growing on say 78% of wood chips will be considered of equal growth ability or virulence as a parent fungus which gives a percentage of 88%. Non-sterile, treated chips will usually show growth in other areas of the chip of other organisms, commonly black coloring fungi, and such background growth coloring may be separately recorded. Such background growth does not change the evaluation being made but does indicate the presence of fungi which have naturally infested the pulpwood.

Deposits

We have deposited with the Northern Regional Research Center (NRRL) at Peoria, Ill., U.S.A. the following fungi referred to herein, which were assigned the Accession Numbers given below along with their date of deposit.

| Fungi | Accession No. | Deposit Date |
| --- | --- | --- |
| C-1D5 (*O. piliferum*) | NRRL 18677 | July 17, 1990 |
| C-1D84 (*O. piliferum*) | NRRL 18678 | July 17, 1990 |
| C-1 (*O. piliferum*) | NRRL 18691 | July 27, 1990 |
| TAB28 (*O. piliferum*) | NRRL 18690 | July 23, 1990 |
| TAB51 (*O. piliferum*) | NRRL 18754 | Jan. 24, 1991 |
| WZ58 (*O. piliferum*) | NRRL 18755 | Jan. 24, 1991 |

The deposits were made under the Budapest Treaty for this application. However, the NRRL were instructed to make generally available to the public, upon deposit, the fungi C-1 and TAB 28.

Experimental

The invention is hereinafter illustrated with reference to a preferred embodiment involving the preferred species *O. piliferum*. In the description below, we employ the fungus we called C-1, a faded (dark gray) isolate of *O. piliferum* obtained from a pulpwood in the State of Virginia, U.S.A. The strain C-1, unlike a number of our *O. piliferum* isolates, is self-fertile. Hence, it was a time-saving candidate as mating could be avoided.

Ascospores of *O. piliferum* are produced in specialized reproductive structures called perithecia. The ascospores are produced in asci within the base of perithecium. As the ascospores mature, the asci autodeliquess and the ascospores are secreted in a droplet of viscous hydrophobic material at the top of the perithecium. Isolation of the ascospores may be effected with pinene as recommended in the literature. However, ascospore isolation was considerably less than desired with pinene and, as an alternative, we found that a sterile vegetable oil/detergent treatment produced a very high degree of the desired dispersal of the ascospores and was non-toxic. In fact, the vegetable oil is consumed by the fungus as an apparent food (carbon source) in a manner judged analogous to the consumption of pitch, and hence the method may be applied to any fungus which consumes pitch. The consumption of the oil was also a very fortuitous manner of eliminating the solvent (oil) for the hydrophobic material.

C-1 was grown on sterile wood for 2–4 weeks to allow for the production of perithecia. Then ascospore drops were picked with a sterile dissection needle and transferred to 400 ul corn oil. The sample was vortexed to form a uniform spore suspension. This suspension was examined in a hemocytometer counting chamber under a microscope and found to contain $1\times10^6$ cells/ml, of which 90–95% were single ascospores. The remaining 5–10% of the fungi consisted of hyphal fragments and clumped ascospores.

The ascospores were diluted 100 fold in sterile corn oil, then two separate additional dilutions, 10 and 100 fold in sterile 10% Triton X100 were made for comparison to each other. 100 ul aliquots of the two dilutions were plated on YMA to achieve plating densities of 100 and 10 spores per plate. Triton X100 was used to disperse the corn oil and prevent reaggregation of the oil droplets on the surface of the agar. Triton X100 is nontoxic to this fungus in liquid culture, but because it was not known how entrapment of spores in oil/detergent micells would effect their germination, a set of dilutions were made without detergent and plated for comparison.

The fungus removed the oil from the plates as it grew. On those plates where spores were plated without detergent, colonies floated on top of the oil and tended to clump. In the presence of oil/detergent, colonies remained discrete and quite compact, but were slower to achieve pickable size. Oil colonies were large enough to pick in 4 days, while oil/detergent colonies were ready in 7 days.

There was no toxicity or prevention of germination observed using the oil/detergent method. The lower viability observed in the absence of detergent may be caused by aggregation of colonies or germinating spores on the oil surface, see table below.

| Method | Colonies per plate | | % Viability |
|---|---|---|---|
| | $10^3$ dilution | $10^4$ dilution | |
| oil | 29, 25, 14, 22, 17, 29 | 2, 9, 3, 1, 2 | 23% |
| oil/detergent | 103, 102, 105, 104, 82, 119 | 10, 5, 10, 12, 8, 8, 9, 14, 10, 9 | 100% |

When the individual colonies were large enough to restreak, all of the colonies from the lower dilution plates, regardless of size or coloration, were transferred to fresh YMA for storage and testing for perithecia production (homokaryon status).

Ascospore Isolation with Pinene

Ten ascospore drops were picked with a sterile dissection needle from a plate of the sporulating fungus and transferred to 400 ul pinene. The sample was mixed to form a uniform spore suspension. A 10 fold dilution in pinene was prepared and 100 ul aliquots of diluted and undiluted suspension were plated on YMA. The pinene was rapidly removed from the open dishes by evaporation in a sterile hood. Single ascospores, hyphal fragments and clumped ascospores in an aliquot of undiluted suspension were counted in a hemocytometer. When individual colonies were large enough all of the colonies were transferred to fresh YMA. Only a few isolated viable colonies were obtained by the pinene method from all attempted isolations, as compared to many hundreds of viable isolated colonies obtained by the oil/detergent method. The following results were obtained during our investigations.

Isolation of Viable Colonies with Oil/Detergent or Pinene

| age of plate | Cells/ml | % single | % viable |
|---|---|---|---|
| | Pinene Method | | |
| 1 week | $28 \times 10^4$ | 50% | 0 |
| 3 weeks | $65 \times 10^4$ | 85% | 0.0008% |
| 4 weeks | $60 \times 10^5$ | 96% | 0 |
| | Corn oil/Detergent Method | | |
| 1 week | $45 \times 10^4$ | 75% | <lim of detection |
| 3 weeks | $28 \times 10^5$ | 98% | 70% |
| 4 weeks | $33 \times 10^5$ | 96% | 69% |

Cells/ml refers to the number of cells in the suspension of 10 ascospore drops picked for the experiment.

Screening for Homokaryons and Preliminary Selection

The C-1 ascospore isolates were screened in order to eliminate as many heterokaryons as possible and to determine the efficacy of the oil/detergent isolation as a method of producing homokaryons. Production of mature perithecia containing ascospores requires two complementary mating types that homokaryotic strains can not possess; heterokaryotic strains may possess both factors (i.e. be self-fertile). Although a homokaryon may produce an immature perithecium, called a protoperithecium, only a heterokaryon may produce a mature perithecium. Thus, heterokaryotic strains can be detected by virtue of perithecium production, but the absence of perithecia formation does not prove a strain to be homokaryotic.

Screening was carried out by streaking each isolate on wood chip agar and monitoring for perithecium production over a 2 month period.

Only 9 out of 105 C-1 isolates screened produced perithecia and were discarded. The following table presents a numeric breakdown of the remaining C-1 isolates that do not produce perithecia and are presumed to be homokaryotic. The isolates were grouped according to the color of growth on wood chip agar.

| Numeric Breakdown of C-1 Isolates | | |
|---|---|---|
| Group Color | Number of Isolates | % of Total |
| black | 29 | 30% |
| grey | 60 | 63% |
| light | 7 | 7% |

The 96 presumed homokaryons obtained from C-1, showed good coverage on wood chip agar. All of the lighter C-1 isolates (and others) were preliminarily screened for growth rate on nonsterile and sterile wood chips in order to select the more virulent of these isolates for further studies.

Growth Screening of More Virulent Light Group Candidates

Each of the more virulent candidate fungi was cultured in YM at room temperature, 200 rpm for 72 hours (72 hours was chosen due to slow grow rate of some strains). Cells were harvested by centrifugation and resuspended in sterile water to a viable CFW concentration of approximately $1\times10^8$/ml.

100 g samples of sterile (autoclaved) and nonsterile (less than 1 week old chips stored at 5° C. prior to use) southern yellow pine chips were inoculated in duplicate with 1 ml of fungal suspension.

The inoculated chips were stored at room temperature in the dark. Growth was monitored with time over a period of ten days.

In the table below, only the evaluation of the five better growing isolates in the light color group are reported. Growth of C1 light isolates.

| Fungus | 1 day | 3 days | 5 days | 7 days | 10 days |
|---|---|---|---|---|---|
| | | | fresh chips | | |
| control | – | – | +/– | +d.g. | +++d.g. |
| C1 parental | – | – | +l.g. | ++l.g. | +++g. |
| C1 oil 6 | – | – | +/– | +l.g. | ++/+++g. |
| C1det5 | – | – | +w. | ++w. | +++/++++l.g. |
| C1det23 | – | – | +/– | ++g. | ++/+++g. |
| C1det41 | – | – | +/– | ++l.g. | +++g. |
| C1det84 | – | – | +w. | +w | +++w |
| TAB28 | – | – | +++d.g. | ++++d.g. | ++++b. |
| | | | sterile chips | | |
| control | – | – | – | – | – |
| C1 parental | – | +/–1 | +++l.g. | ++++l.g. | ++++l.g. |
| C1 oil 6 | – | +/–w | + | +++l.g. | ++++l.g. |
| C1det5 | – | ++w. | +++w. | ++++l.g./w | ++++l.g. |
| C1det23 | – | +/–w. | ++w. | +++g. | ++++l.g. |
| C1det41 | – | +/–l. | ++l.g. | +++/++++l.g. | ++++l.g. |
| C1det84 | – | +w | ++w | +++/++++w. | +++/++++w. |
| TAB28 | – | ++d.g. | ++++d.g. | ++++b. | ++++b. |

The above homokaryons isolates indicated a range of virulence, with at least C1 det 5 and C1 det 84 indicated to meet our criteria.

Pitch Reduction and Brightness Effects

Fungi was cultured in YM at room temperature, 200 rpm for 72 hours. Cells (about 95% blastospores/5% mycelia) were harvested by centrifugation and resuspended in sterile water to approximately a viable CFU of $1\times10^8$/ml. Five replicate 100 g bags of sterile southern yellow were inoculated with 1.0 ml of fungal suspension. The inoculated and control bags were incubated at room temperature in the dark for three weeks. Four replicates from each set of five were analyzed for pitch content. The fifth was measured for brightness. Results are given in the table below.

| Sample | Color of growth on wood | % Extractives | Brightness |
|---|---|---|---|
| Control | not applicable | 1.81 | 49.5 |
| C-1 parental | gray | 0.90 | 38.3 |
| C-1det69 (Gray Group) | gray | 1.15 | 41.2 |
| C-1det2 (Gray Group) | gray | 0.83 | 44.7 |
| C-1det5 | light gray | 0.88 | 46.8 |
| C-1det84 | white | 1.38 | 51.9 |
| C-1det90 (Black Group) | black | 1.49 | 24.0 |

All the above tested strains showed significant pitch reduction. The degree of brightness loss depended upon the color of growth of the fungus on wood. The two light strains tested C-1 det 5 (C-1D5) and C-1 det 84 (C-1D84) showed considerably better brightness than the parent C-1 fungus. The C-1D84 desirably was indicated to have better brightness than the untreated control.

A number of faded ascospore isolates were tested for growth under field conditions (non-sterile wood chips).

Fungal strains were inoculated with a hand-held sprayer on non-sterile wood chips prepared from 2 day old logs to form 10 ton piles. The non-sterile chips were obtained from an area in which a native *O. piliferum* blue stain had been tolerated and were selected on the basis of being naturally infested with such blue stain. The piles were incubted outside under ambient conditions, for two weeks. The piles were then dismantled and the amount of fungal growth was recorded.

The table below summarizes the results of this field trial comparing faded strains inoculated with a hand held spryer.

| Treatment (Group) | Dose CFU/kg chips | Average growth Background | Light |
|---|---|---|---|
| control | | ++++ | |
| TAB28 (black) | $2 \times 10^8$ | ++++ | |
| C1det2 (gray) | $3 \times 10^8$ | ++++ | ++/+ |
| C1det4 (gray) | $9 \times 10^8$ | ++++ | + |
| C1det23 (light) | $2 \times 10^7$ | ++++ | + |
| C1det23 (light) | $2 \times 10^8$ | ++++ | ++ |
| C1det41 (light) | $3 \times 10^7$ | ++++ | + |
| C1det41 (light) | $3 \times 10^8$ | ++++ | +/+ |
| C1det72 (gray) | $4 \times 10^8$ | ++++ | +/+ |
| C1det84 (white) | $4 \times 10^7$ | ++++ | +++ |
| C1det84 (white) | $4 \times 10^8$ | ++++ | +++/+ |
| C1det5 (light) | $5 \times 10^8$ | ++++ | +++ |
| C1det5 (light) | $5 \times 10^9$ | ++++ | +++ |

Dosage applied is expressed as colony forming units (CFU) per kg of wood chips. Background growth is indicative of growth of black/dark colored fungi already present in the wood (or of inoculum in the case of the black strain TAB28).

In addition, C-1D5 was inoculated with an in-line sprayer on chips prepared from 3 week old logs and the results of growth on 10 ton piles are given below (which also indicates a potential suppression of backgroud growth by the fungus).

| Treatment | Dose CFU/kg chips | Average growth Black | Light |
|---|---|---|---|
| control | | +++/+ | |
| C1det5 | $7 \times 10^7$ | +++ | +++ |
| C1det5 | $4 \times 10^8$ | ++/+ | ++++ |

Both C-1D5 ad C-1D84 showed very good growth on the non-sterile chips and also a dose/response relationship.

The above results indicate, in addition to the good pitch reduction and essentially the absence negative brightness influence, that the selected isolates C1det84 and C1det5 grow very well under the highly competitive conditions which may be encountered in a wood chip pile or other pulpwood forms, and in particular produce their desired effect at inoculum dosages approaching the same order of magnitude as the highly effective TAB28. Not only are such objectives met by these two species, but the results indicate the additional and most significant advantage in the potential of such fungi to partially overcome or displace the darkening influences of fungi which naturally infect such pulpwoods, thereby resulting in a pulpwood which is essentially even lighter than a control or conventionally handled pulpwood, thus potentially allowing even a reduction in subsequent treatments used to enhance brightness as particularly applied, for example, in connection with mechanical pulps.

The white growing ascospore fungus Cldet84 and a black growing wild type *O. piliferum* fungus TAB 51 were mated together by streaking cultures of each from YMA plates over the same area of woodchip agar plate and then incubating the streaked culture plate for four (4) weeks on the bench after covering the plate with parafilm. Ascospores from the mating were isolated and recovered by the procedure described above (oil/detergent isolation), and then approximately 93 isolates were grown up and preliminarily evaluated as to color and growth virulence. Three (3) of the candidates, herein WZ19, WZ24 and WZ58 were selected for further evaluation on the basis of their white color and excellent growth characteristics (all three exhibited a growth virulence similar to TAB28 which itself is superior to TAB 51 in growth virulence). TAB51 exhibits the dark blue or essentially black color of the typical blue stain fungi when grown on a wood substrate, eg. sterilized or non-sterile southern yellow pine.

The three candidates were then grown up to produce inoculum and evaluated from growth as described above under the heading Growth Screening of More Virulent Light Group Candidates, along with others for comparison, the results on southern yellow pine non-sterile wood chips being reported below.

| O. piliferum strain | Inoculated fungal growth | | | |
|---|---|---|---|---|
| | 4 days | 6 days | 8 days | 10 days |
| Control | − | − | +/− | +/− |
| TAB28 | +/++ | +++/++++ | ++++ | ++++ |
| C1det5 | + | ++ | +++/++++ | ++++ |
| C1det84 | + | ++ | +++/++++ | ++++ |
| WZ19 | +/− | +++/++++ | ++++ | ++++ |
| WZ24 | +/++ | +++/++++ | ++++ | ++++ |
| WZ58 | ++ | +++/++++ | ++++ | ++++ |

The three candidates were then evaluated as to pitch reduction and brightness effects according to the method previously described under the heading Pitch Reduction and Brightness Effects, except that the treated substrates were incubated for only two weeks. The results on southern yellow pine sterile wood chips are reported below.

| Strain | Color of growth on wood | % Extractives | Brightness |
|---|---|---|---|
| Control | Not applicable | 3.2 | 34.5 |
| TAB28 | Black | 2.0 | 25.0 |
| C1det5 | Light gray | 2.6 | 34.6 |
| C1det84 | White | 2.3 | 37.6 |
| WZ19 | White | 2.1 | 35.9 |
| WZ24 | White | 2.1 | 37.1 |
| WZ58 | White | 2.1 | 35.9 |

Growth on Non-Sterile Wood Chips Under Field Conditions

Fungal strains were inoculated with a hand-held sprayer on non-sterile southern yellow pine wood chips prepared from a mixture of 40% seasoned logs (2–3 months old) and 60% fresh wood (approximately 3 weeks old) and stored in 10 ton chip piles. Chips were inoculated at a dose of $2 \times 10^{11}$ CFR/ton (about $9.09 \times 10^7$ CFU/Kg.) as they were being dumped off a front end payloader onto heating platforms in the chipyard. Heating platforms consisted of 2 foot tall cinderblock walls supporting a frame constructed of 2×4 planks. Heavy duty chicken wire was stapled to the 2×4 planks to provide support for the wood chips. A thermostatically controlled forced air heater was placed under each heating platform and set to maintain air temperature at 75° C. The piles were incubated under these conditions for 10 days. The piles were then dismantled for evaluation. The average amount of fungal growth throughout the interior of the pile was recorded. Samples were taken from the center of the piles and analyzed for pitch content and brightness. The results are reported below.

| Sample | Average Growth | | % Extractives | Brightness |
|---|---|---|---|---|
| | Background | Light | | |
| Control | +/− | +/− | 3.7 | 33.5 |
| C1det5 | +/− | + | 2.8 | 34.2 |
| WZ19 | +/− | +++/++++ | 2.7 | 32.9 |
| WZ24 | +/− | ++ | 3.6 | 32.9 |
| WZ58 | +/− | ++++ | 2.3 | 33.5 |

The strain exhibiting the best overall growth rate, WZ58, also reduced pitch levels to the lowest value. Background growth is indicative of growth of black/dark colored fungi already present on the wood.

The penetrating fungus used in the present invention are judged a recognizable type of fungi. Penetrating stain fungi were recognized by Boyce, Forest Pathology, Third Edition, 1961, McGraw-Hill Book Company, Chapter 20, pages 493–512, particularly 496–497, as causing a deep stain that cannot be readily planed off. Such fungi may also be generally characterized by colonization of the xylary tissues of non-sterilized wood, Boyce, supra, pages 499–504. Microscopic analysis indicates that such fungus are characterized by both invading and depositing color or staining the ray parenchyma cells and, in the case of at least softwoods, in the resin ducts. Hence, the distinction between surface penetrating and the true penetrating fungi of the invention may be fairly readily ascertained different ways, eg. by close or microscopic examination of cross-sections of unrefined (but debarked) pulpwood taken in the area of an inoculation and after a set time of reasonable growth at essentially an optimal growth temperature of the fungus. Staining or the deposit of mycelia residue well within the parenchyma cells (and resin ducts in the case of softwoods) is caused by the penetrating fungi. When the penetrating fungi does not visably stain, its presence may also be observed, eg. by the mycelia deposits. In either case, a degradation effect upon the pitch in the cells and ducts may be determined, if needed, by microscopic examination, eg. by SCM (Scanning electromicroscope) and confirmed by assaying for pitch reduction by a standard method as indicated herein. Various evaluations may also be made by growing the fungus. In general, the suitable fungi will exhibit substantial growth at temperatures in the range of 40° F. to 90° F. and for evaluation purposes a temperature of optimal growth will be selected. Such evaluations may be made, for example, using a debarked pulpwood such as a log with diameter of about 12 inches which is freshly cut and appears uninfected by organisms, and on which the fungus exhibits its natural growth. The fungus is preferably inoculated in a lightly sanded area and wood specimen maintained at the predetermined optimal growth temperature and a constant humidity of about 90% for three weeks or more depending upon growth rate. Inoculation rates will be increased to very high levels to expedite or induce growth of slower growing fungi. Cross sections can be taken, and the penetrating fungi are generally those in which one or more of three cross-sections show a discoloration or other penetration of fungal growth at least 6 mm or more below the inoculated surface. The preferred such fungi are those which penetrate to a depth considerably greater than 6 mm and desirably which on close or microscopic inspection show not only a substantial invasion of parenchyma cells but also a substantial reduction or essentially avoiding of the resin content normally found within such cells. For classification purposes, the evaluations are conducted on specimens of a pulpwood which is more commonly subject to natural infection by the fungus to be evaluated.

The term "pulpwood" as used herein means any harvested (cut down) form of a tree material used in making paper, cardboard or other cellulosic product such as viscose, but prior to pulping,, and includes such forms as timber, logs, wood chips, sawdust and the like. The term "refined pulpwood" means a pulpwood resulting from the application of mechanical and/or shearing forces to whole pulpwood forms such as logs to obtain a multiplicity of high surface area, small pieces, such as wood chips and sawdust, which are introducible into a pulping process. The term first stage mechanical pulp means a pulp, isolated from a mechanical pulping process, which contains 60% or more of the lignin content of the substrate prior to pulping.

The fungi provided by the invention may be used to reduce the ptich content of pulpwoods and first stage mechanical pulps as described in said U.S. application Ser. No. 310,814, filed Feb. 13, 1989. Basically, an inoculum of at least one of the fungus is applied to the substrate(s) and the inoculated substrate(s) maintained at a growth temperature of the fungus, e.g. 35°–90° F., for a time sufficient to degrade the pitch content of the substrate, e.g. 7–14 days. Refined pulpwoods are generally accumulated, e.g. in a pile, after inoculation which will be desirably representatively distributed throughout the accumulation. Such accumulation may be in the form of a typical wood chip pile or in a container or enclosed space such as a rail car, ship or the like to allow pitch reduction to be effected during transport. Timber, logs and the like may be treated in many fashions to induce growth in a major portion or more of such substrate, e.g. timber or logs may be scored lengthwise and the inoculum applied in the scoring, or even the cut ends may be inoculated. First stage mechanical pulp is a sterilized substrate and the invention may be applied generally to both sterilized and non-sterile substrates. However, particular and desired benefits are of course to be realized when the invention is used with non-sterile pulpwoods, including non-sterile refined pulpwoods. Dosage applied in practice of the present invention will not exceed $10^{10}$ CFU/Kg. of substrate with refined pulpwoods, and preferably are not in excess of $10^9$ CFU/Kg., and lower dosages may be used with more preferred embodiments.

In-Line Sprayer

The in-line spray system for dispensing inoculum in large scale operations includes a 50 gallon tank, a motor driven propeller, and a pump. The 50 gallon tank acts as a reservoir of inoculum. A propellor inside the tank is used to provide the agitation required to keep the fungal cells in suspension. The pump withdraws the inoculum from the reservoir and dispenses the liquid at a rate of 25 gallons/minute to a series of 7 nozzles connected to best effect uniform discharge from each nozzle. The nozzles are attached 3 feet above a screw type conveyor having four one foot diameter screws in paralled across a bed which is five feet wide and four feet deep. The seven nozzles are organized in staggered fashion in two rows of four and three nozzles with 1.5 feet separating the two rows. The chips are advanced at about 60 feet/minute. The inoculated chips are discharged from the belt for evaluation storage at a point four feet passed the last (3 nozzle) row.

Fermentation and Formulation

Cells (blastospores) of WZ-58 are fermented at 25° C. (10 liter Chemap fermentor) in media containing 200 g. per liter malt extract and 20 g. per liter yeast extract until cell density is $3 \times 10^9$ cells/mi. The fermentation media (CA.36–48 hours) aerated (oxygen levels near saturation, ie. not limiting at any point during fermentation).

The biomass grown in the fermentor is harvested by centrifugation and the pelleted cells mixed with clay at a ratio of 1 part wet biomass (approximately 20% solids) to 2 parts dry Kaolin clay. The moisture content of the biomass-:clay mixture ranges from 25–30%. The flowable mixture is loaded into an Aeromatics fluid bed dryer and subjected to drying under ambient temperature conditions to a final moisture content of 5–10%. Outlet air temperature is maintained below 35° C. Drying time is from 20–40 minutes. Fluid bed dried material retains viability and the ability to grow on non-sterile wood chips and reduce pitch levels after prolonged storage at –15° C.

TABLE

Stability of fluid bed dried biomass stored at –15° C.

| Storage time (Days) | Colony forming units/gram |
| --- | --- |
| 0 | $2 \times 10^{10}$ |
| 24 | $2 \times 10^{10}$ |
| 67 | $1 \times 10^{10}$ |
| 107 | $6 \times 10^9$ |
| 178 | $5 \times 10^9$ |

What is claimed is:

1. A pulpwood treated with a homokaryotic wood-penetrating, pitch-degrading fungus of the genus Ophiostoma and embodying sufficient natural infestion by *heterokaryotic* native pulpwood coloring fungi that the brightness of the non-sterilized, untreated pulpwood prior to treatment is reduced by at least 10% compared to the sterilized, untreated pulpwood when each are maintained for comparison at room temperature over the lesser of 14 days or the period during which the pulpwood was fungus-treated, said treated pulpwood having a brightness level at least as great as the brightness level exhibited by said non-sterilized and untreated pulpwood after said non-sterilized, untreated pulpwood was maintained at room temperature for the period during which the pulpwood is fungus-treated.

2. Pulpwood in accord with claim 1 which is pinewood.

3. Pulpwood in accord with claim 2 which is southern (United States) yellow pinewood.

* * * * *